(12) United States Patent
Stradella

(10) Patent No.: US 7,299,800 B2
(45) Date of Patent: Nov. 27, 2007

(54) FLUID PRODUCT DISPENSING DEVICE

(75) Inventor: Giuseppe Stradella, Camogli (IT)

(73) Assignee: Valois S.A.S., Neubourg (FR)

( * ) Notice: Subject to any disclaimer, the term of this patent is extended or adjusted under 35 U.S.C. 154(b) by 383 days.

(21) Appl. No.: 10/500,329

(22) PCT Filed: Dec. 23, 2002

(86) PCT No.: PCT/FR02/04533

§ 371 (c)(1),
(2), (4) Date: Jan. 4, 2005

(87) PCT Pub. No.: WO03/055548

PCT Pub. Date: Jul. 10, 2003

(65) Prior Publication Data

US 2005/0109336 A1 May 26, 2005

(30) Foreign Application Priority Data

Dec. 28, 2001 (FR) ................................... 01 17027

(51) Int. Cl.
*A61M 11/00* (2006.01)
(52) U.S. Cl. .............................. 128/200.23; 128/203.12
(58) Field of Classification Search ........... 128/200.14, 128/200.23, 200.18, 203.12, 203.13, 203.15
See application file for complete search history.

(56) References Cited

U.S. PATENT DOCUMENTS

| | | | |
|---|---|---|---|
| 5,027,808 A * | 7/1991 | Rich et al. ............. | 128/203.23 |
| 5,826,571 A | 10/1998 | Leith et al. | |
| 6,328,035 B1 * | 12/2001 | Wakefield et al. ..... | 128/203.23 |
| 6,553,988 B1 * | 4/2003 | Holroyd ................. | 128/200.23 |
| 6,866,037 B1 * | 3/2005 | Aslin et al. ............ | 128/200.23 |
| 7,093,594 B2 * | 8/2006 | Harrison et al. ....... | 128/203.15 |

FOREIGN PATENT DOCUMENTS

| | | |
|---|---|---|
| GB | 2 323 041 A | 9/1998 |
| WO | WO 01/70319 A | 9/2001 |
| WO | WO 02/41939 A | 5/2002 |

\* cited by examiner

*Primary Examiner*—Steven O. Douglas
(74) *Attorney, Agent, or Firm*—Sughrue Mion, PLLC

(57) ABSTRACT

A fluid dispenser device including a reservoir containing the fluid and a propellant; a metering valve mounted on the reservoir and including a metering chamber, and a valve member that is movable between a rest position and a dispensing position; and an automatic trigger system, the trigger system including an actuator element to displace one of the valve member and the reservoir relative to the other so as to bring the valve member into its dispensing position. The device also includes a brake system which co-operates with the reservoir or the valve member to slow down displacement of the valve member towards its dispensing position while the device is being actuated, and a valve-member release system that is actuated automatically when the valve member reaches its dispensing position, and which returns the valve member to its rest position independently of the position of the actuator element.

10 Claims, 3 Drawing Sheets

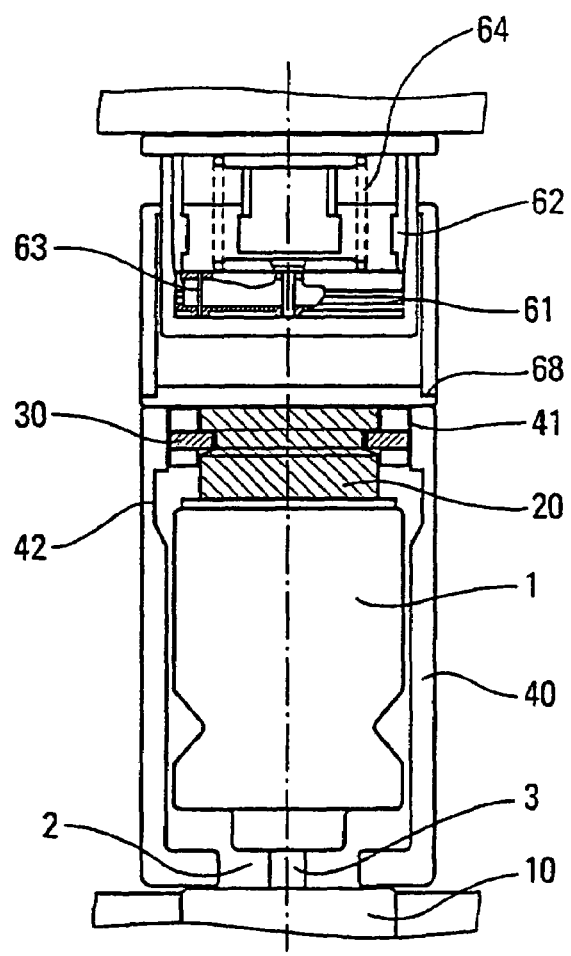
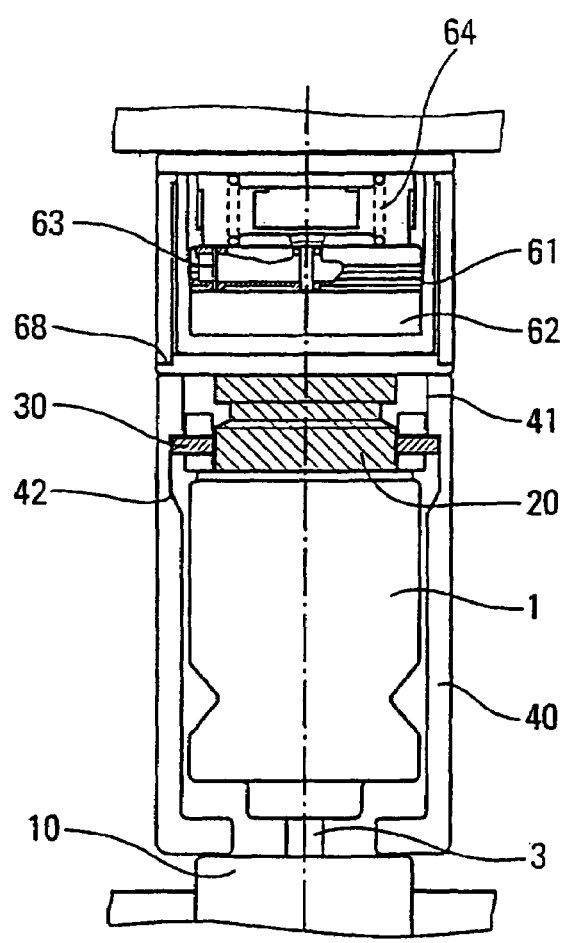
Fig. 1
Fig. 2

FLUID PRODUCT DISPENSING DEVICE

BACKGROUND OF THE INVENTION

The present invention relates to a fluid dispenser device, and more particularly to an inhalation device including a metering valve, the device being of the "Metered Dose Inhaler" (MDI) type, in which actuation of the metering valve is controlled by the user inhaling.

Such inhalation-actuated MDI inhalers, generally referred to as "Breath-Actuated Inhalers" (BAI) using metering valve systems are usually based on a trigger mechanism including a spring, said spring being released by an appropriate device when the user inhales. The spring is usually loaded or compressed by actuating a lever, e.g. while opening the lid of the inhaler mouthpiece, and the force of the spring is directed, at the time of inhalation, against the metering valve of the inhaler, or against the reservoir, enabling the valve to be actuated by displacing the valve member relative to the reservoir. This is made possible as a result of that one of the elements from amongst the valve member and the reservoir, that is not subjected to the action of the previously loaded spring, being held stationary inside the device. Once the metering valve has been actuated, and once the fluid contained in the reservoir has been dispensed, said metering valve generally remains compressed, with the valve member in its actuated position, until the load from the spring is relaxed, which can only occur when the lid of the mouthpiece is closed.

The above-described structure is the source of a problem which is linked to the way in which most metering valves operate. The valves generally include a return spring, and a metering chamber which is filled by the mixture constituted by fluid, generally a medicine, and a liquefied propellant gas. The metering chamber is filled by gravity, and only when the valve member is displaced from its dispensing position to its rest position, i.e. when the force applied on the valve by the spring of the trigger system is relaxed. This therefore implies that the tension of the spring must be released when the device is in a position that is appropriate to enable the metering chamber of the valve to be filled by gravity. The position required for the metering chamber to be filled effectively and completely is the working position of the inhaler, in which the reservoir is generally disposed above the metering valve, the user having the mouthpiece in the mouth so as to breath in the dose of dispensed fluid.

Once the dose of fluid has been dispensed, when the user removes the device from the mouth, there is a high probability that the inhaler is no longer in the position required for effective filling, and there is a high risk of the user closing the lid of the mouthpiece while the inhalation device is in an inappropriate position for filling the metering chamber completely.

Systems have therefore been proposed for releasing the valve member, and enabling it to be returned automatically to its rest position, independently of any intervention by the user. Such systems generally include means that are actuated when the valve member reaches its dispensing position, and which enable the valve member to return immediately to its rest position, and therefore enable the metering chamber to be filled in the appropriate position. Document U.S. Pat. No. 5,826,571 discloses such a system.

The use of such valve-member release systems can however lead to other drawbacks.

It is necessary to allocate enough time to enable the entire dose to be expelled from the metering chamber during actuation. Unfortunately, in general, the fluid is dispensed when the inlet orifice of the valve member is inside the metering chamber. This takes place at the end of the actuating stroke of the valve member and at the start of its return stroke towards its rest position. Thus, the valve-member release systems, which return said valve member to its rest position as soon as it has reached its dispensing position, risk reducing the time taken to empty the metering chamber to too great an extent. In other words, the valve member risks being released and returned to its rest position before the entire dose has been dispensed. The accuracy of dose metering can be affected thereby, which can have very serious consequences, in particular with certain pharmaceuticals whose effectiveness is linked directly to the accuracy with which the doses are dispensed. Document WO 01/70319 discloses a device including means for temporarily blocking the valve member in the dispensing position. The system presents the drawback of keeping the valve open during said temporary blocking, thereby presenting a risk if the user moves the device before the valve closes.

BRIEF SUMMARY OF THE INVENTION

An object of the present invention is to provide a fluid dispenser device which does not reproduce the above-mentioned drawbacks.

An object of the present invention is therefore to provide a fluid dispenser device which guarantees that the metering chamber of the valve is completely emptied at each actuation.

Another object of the present invention is to provide a fluid dispenser device which guarantees that the metering chamber of the valve is completely filled after each actuation.

Another object of the present invention is to provide such a fluid dispenser device which enables the metering chamber of the metering valve to be completely filled and completely emptied, independently of the user.

Another object of the present invention is to provide such a fluid dispenser device which is simple and inexpensive to manufacture and to assemble.

The present invention therefore provides a fluid dispenser device comprising: a reservoir containing the fluid and a propellant; a metering valve mounted on said reservoir and comprising a metering chamber, and a valve member that is movable between a rest position and a dispensing position; and an automatic trigger system, preferably actuated by the user inhaling in order to actuate said valve, said trigger system including an actuator element adapted to displace one of the valve member and the reservoir relative to the other so as to bring the valve member of the valve into its dispensing position, the device being characterized in that it includes, in combination, a brake system which co-operates with the reservoir or with the valve member in order to slow down displacement of the valve member towards its dispensing position while the device is being actuated, and a valve-member release system that is actuated automatically when the valve member reaches its dispensing position, and which returns said valve member to its rest position independently of the position of said actuator element.

Preferably, said brake device is pneumatic and/or hydraulic.

In a first embodiment, said brake device comprises a piston connected to said actuator element by means of a control element, said piston sliding in sealed manner in a chamber, said chamber or said piston being provided with a small passage so that the gas or liquid can flow only slowly into or out of said chamber, ensuring that said piston is displaced slowly.

In a second embodiment, said brake device comprises a piston connected to said actuator element by means of a control element, said piston sliding in non-sealed manner in a chamber so that the air contained in the chamber can flow only slowly out of said chamber, ensuring that said piston is displaced slowly.

Preferably, said valve-member release system includes a blocking element co-operating with one of the valve member and the fluid reservoir, said blocking element being movable between a blocking position, in which the valve member can be brought into its dispensing position by said actuator element of the trigger system, and an unblocking position, in which the valve member is returned to its rest position independently of the position of said actuator element, said blocking element being urged towards its unblocking position after the trigger system has been actuated, when the valve member reaches its dispensing position.

The valve-member release system advantageously includes a retaining member that is displaceable between a retaining position, in which it retains said blocking element in its blocking position, and a non-retaining position, in which it does not retain said blocking element in its blocking position, said retaining member being displaced towards its non-retaining position when the valve-member reaches it dispensing position.

Said valve-member release system advantageously includes a control element co-operating firstly with the valve member and/or with the actuator element, and secondly with said retaining member, so that when the valve member reaches its dispensing position, the control member makes it possible to displace the retaining member into its non-retaining position, so that the blocking element is displaced towards it unblocking position and the valve member is returned to its rest position by the return spring of the valve.

Advantageously, said retaining member is elastically deformable, and said control element includes a first inside diameter co-operating with the retaining member so as to prevent it from deforming, and thus hold it in its retaining position, and a second inside diameter that is greater than said first inside diameter, which co-operates with said retaining member when the valve member reaches its dispensing position, thereby enabling said retaining member to deform towards its non-retaining position.

Said retaining member advantageously includes one or a plurality of elastically deformable tabs.

The second-diameter portion of the control element is advantageously formed by one or a plurality of openings adapted to co-operate with the retaining member.

BRIEF DESCRIPTION OF THE SEVERAL VIEW OF THE DRAWINGS

Other characteristics and advantages of the present invention appear more clearly from the following detailed description of two embodiments thereof, given by way of non-limiting example, and described with reference to the accompanying drawings, in which:

FIG. 1 is a diagrammatic section view of a fluid dispenser device constituting a first embodiment of the present invention, before the valve has been actuated;

FIG. 2 is a view similar to that of FIG. 1, after the valve has been actuated;

DETAILED DESCRIPTION OF EXEMPLARY EMBODIMENTS OF THE INVENTION

Figure 3:
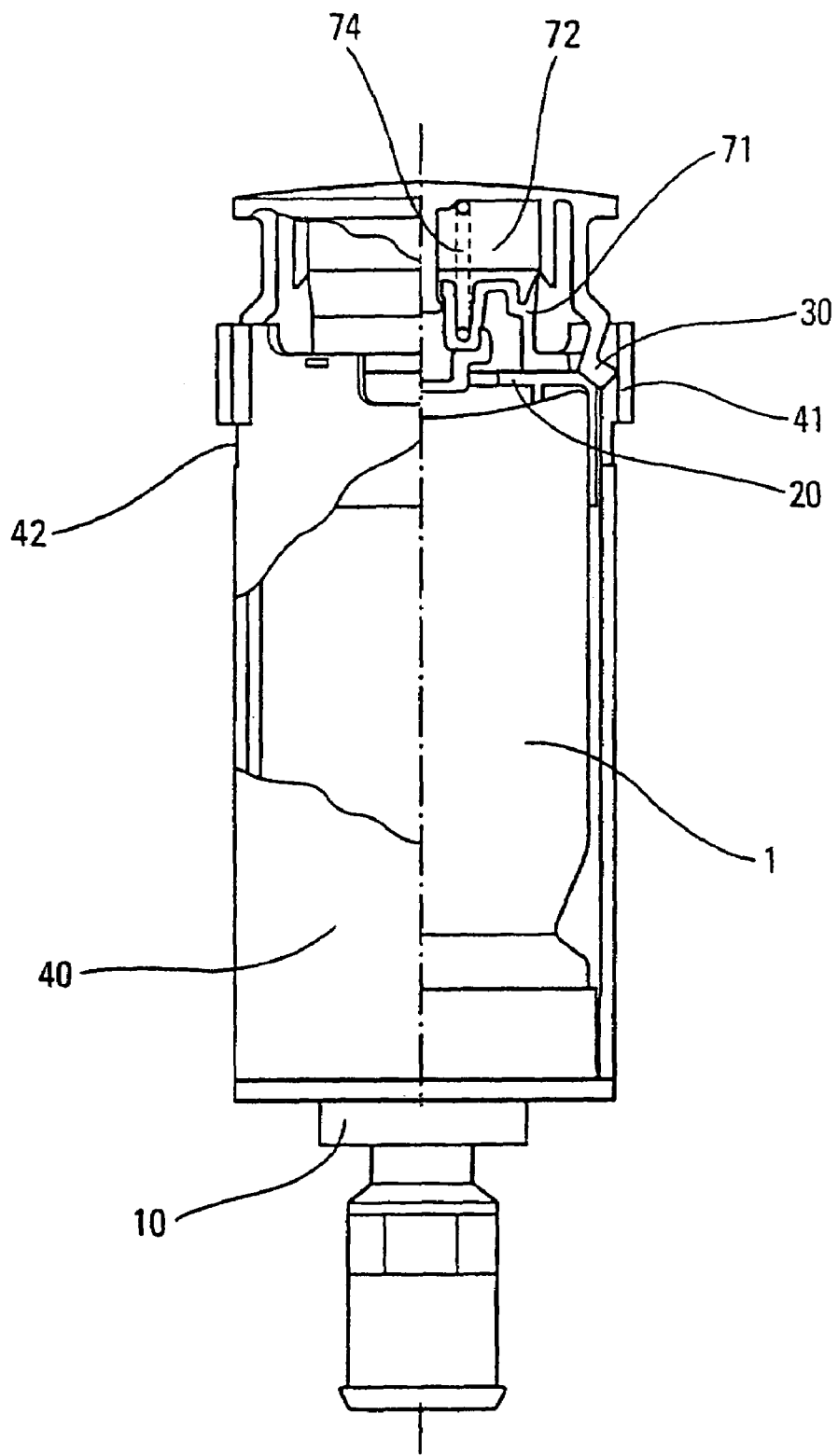
FIG. 3 is a partially cut-away diagrammatic section view of a second embodiment of the invention, before the valve has been actuated.

The present invention applies to any type of inhaler that is triggered by the user inhaling (BAI), and even if the description of various embodiments is made in connection with an inhaler in which the inhalation trigger system acts on the valve member, it is clear that the invention also applies to devices in which the spring acts on the reservoir. Whether the resilient actuating force of the valve is exerted on the valve member or on the reservoir has no direct influence on the present invention which applies in both cases, the purpose of the present invention being to slow down displacement of the valve member towards its dispensing position.

The following description is therefore made with reference to a device of the type disclosed in document WO 99/44662, that document being incorporated by way of reference in the present invention with regard to the operation of the inhalation trigger system of the fluid dispenser device.

In the invention, a brake device is provided that acts on that one of the elements from amongst the valve member and the reservoir that is subjected to the resilient force of the actuator element 10 of the trigger system, i.e. on the element that is displaced during actuation. The brake device therefore makes it possible to slow down, in predetermined manner, displacement of the portion of the BAI that is movable while the valve is being actuated.

FIGS. 1 and 2 show a first embodiment in which the brake is a pneumatic brake 60. The brake 60 comprises a piston 61 connected to a control element 40 which co-operates with the actuator element 10. The control element 40 can either be directly connected to said piston 61, or an intermediate element 68 can be provided that co-operates firstly with the control element 40, and secondly with the piston 61, as shown in FIGS. 1 and 2. Said piston 61, which preferably includes an elastomer coating, slides in sealed manner in a chamber 62, said chamber 62 or said piston 61 being provided with a small passage or an orifice 63 of small diameter.

In the example shown in FIGS. 1 and 2, the brake 60 operates by suction, i.e. in the rest position shown in FIG. 1, the piston 61 is disposed against the end wall forming the chamber 62. When the user actuates the device, the actuator element 10 of the trigger system acts on the control element 40, which causes the piston to move away from the end wall of the chamber 62, creating suction between said end wall and said piston 61, the small-diameter orifice 63 enabling air to penetrate into said chamber 62 at slow speed only. Thus, said piston 61, and therefore the valve member 3, can only be displaced slowly, thereby ensuring the required braking. Naturally, the effectiveness of the brake depends on the dimensions of the orifice 63 and of the chamber 62.

Advantageously, the pneumatic brake is also provided with a return spring 64 which enables the piston to return to its start position when the actuator element 10 of the trigger system is returned to its rest position (in particular by closing the lid).

Although the example of the pneumatic brake is described above with reference to a system operating by suction, it is clear that the pneumatic brake of FIGS. 1 and 2 can be made in such a manner as to operate by compression. In this case, in the rest position, the piston 61 would be at a distance from the end wall of the chamber 62, and when the device is actuated, it would be urged resiliently towards said end wall, so that the air contained inside the chamber 62 could escape only through said small-diameter orifice 63, and at slow speed only, thereby providing the required braking.

In addition, it is also possible to envisage making the brake system in hydraulic manner, by replacing the air with any desired liquid, and by adapting, in corresponding manner, the dimensions of the chamber 62 and of the small-diameter orifice 63.

In a variant, it is also possible to use a gear system enabling the desired braking function to be provided.

Figure 4:
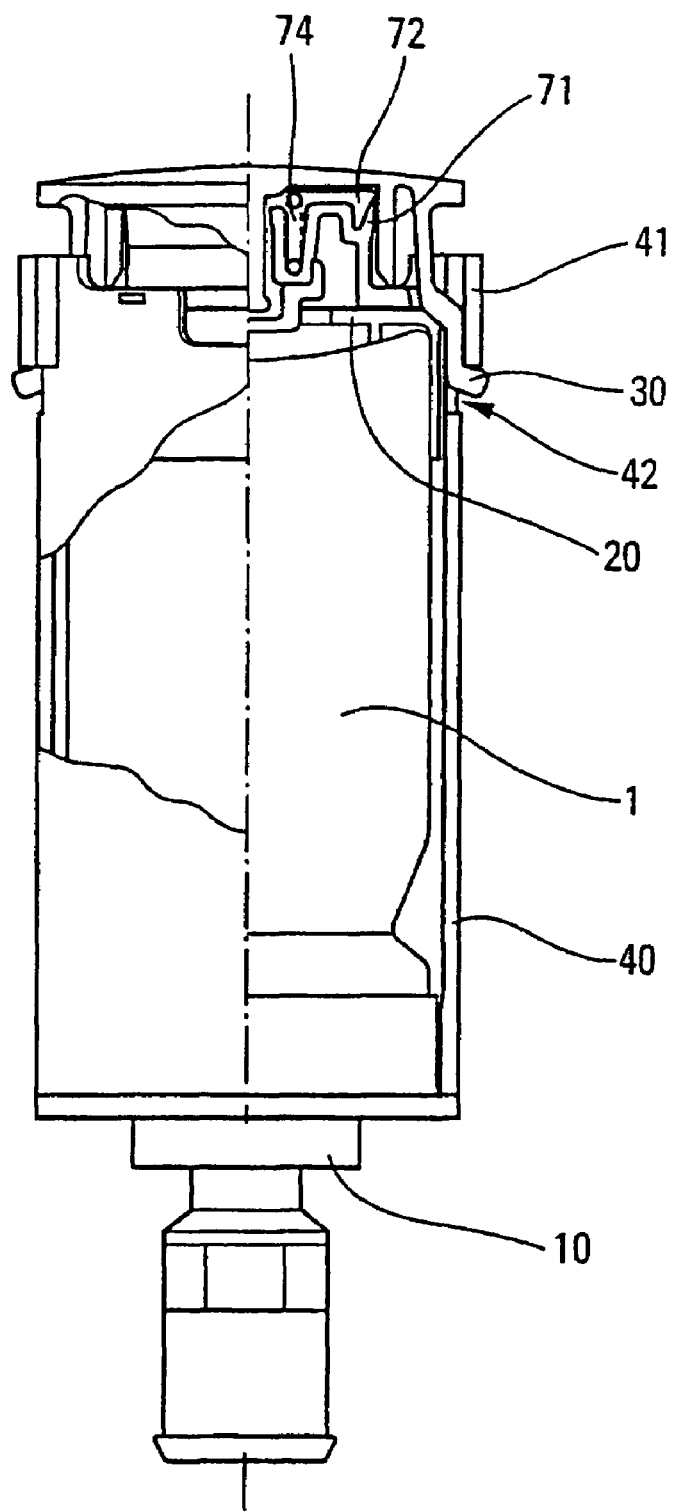
FIG. 4 is a view similar to that of FIG. 3, after the valve has been actuated.

FIGS. 3 and 4 show a second embodiment of the brake device in which the brake 70 includes a piston 71 sliding in non-sealed manner in the chamber 72. Preferably, the piston 71 does not include an elastomer gasket, and an escape passage is formed between the piston 71 and the chamber 72, the air contained in the chamber 72 thus being able to flow slowly out of said chamber through said escape passage. Advantageously, the piston 71 also includes a return spring 74. The example in FIGS. 3 and 4 is therefore a compression brake. This is advantageous because the effectiveness of the brake is thus at a maximum at the end of the actuating stroke of the valve member 3, i.e. when the valve member enters into communication with the metering chamber of the valve. The end of the actuating stroke of the valve member 3 is therefore braked in very effective manner, thereby correspondingly extending the time during which the metering chamber can be emptied. The metering chamber is thus emptied completely at each actuation, and optimal metering accuracy is therefore achieved, even with the use of a valve-member release system as described below.

In the invention, the brake system described above with reference to FIGS. 1 to 4 is advantageously combined with a valve-member release system acting automatically as soon as the valve-member 3 reaches its dispensing position. This combination makes it possible to ensure that the valve-member returns automatically to its rest position immediately after each actuation, so as to guarantee that the metering chamber of the valve is filled completely and reliably.

With reference to FIGS. 1 and 2, a first variant embodiment of such a valve-member release system is described below.

FIG. 1 diagrammatically shows a fluid reservoir 1 on which a metering valve 2 is mounted in any desired manner, said metering valve 2 including a valve member 3 that is movable between a rest position and a dispensing position. The metering valve 2 includes a metering chamber (not-shown) which is emptied when the valve member 3 is in its dispensing position, and which is filled by gravity when the valve member 3 returns from its dispensing position to its rest position. Said valve member 3 co-operates with an actuator element 10 which preferably forms part of an inhalation trigger system, and which is constituted by, or is secured to, a spring (not shown in FIGS. 1 and 2), said spring being able to be loaded by the user before the device is used, so that during inhalation, the actuator element 10 is released and can exert a force on the valve member 3 in order to actuate the metering valve. During this process, during which the valve member 3 is displaced from its rest position to its actuated position, the reservoir 1 is held fixed in the body of the device.

The valve-member release system includes a blocking element 20, which, in the example in FIGS. 1 and 2, co-operates with the end wall of the reservoir 1. The blocking element 20 is retained in its blocking position by a retaining member 30, which, in the example shown in FIGS. 1 and 2, is made in the form of a split ring that is deformable radially outwardly. The split ring 30 co-operates with said blocking element 20 so as to hold it in its blocking position, in which it holds the reservoir 1 fixed inside the device. A control element 40, which is advantageously the same as the control element of the above-mentioned brake, is firstly connected to the actuator element 10 of the trigger system, and secondly co-operates with said retaining element 30. Thus, as can be seen in FIGS. 1 and 2, the control element 40 is displaced at the same time as the actuator element 10, and therefore at the same time as the valve member 3 when the metering valve is actuated. The control element 40 can be made in the form of a sleeve which externally surrounds said retaining member 30, and includes a first diameter 41, and second diameter 42 that is greater than said first diameter. The first diameter 41 of the control element 40 co-operates with the retaining member 30 before the device is actuated, and the second diameter 42 co-operates with said retaining member 30 after the device has been actuated, when the valve member 3 is in its dispensing position. At this moment, the retaining member 30 can deform radially outwardly inside the second diameter 42 of the control element 40 so as to release the blocking element 20. The blocking element 20 can then slide axially under the effect of the force exerted by the return spring (not shown) of the metering valve, so that said metering valve returns to its rest position as soon as the retaining member 30 is displaced towards its non-retaining position shown in FIG. 2. The valve member 3 remains blocked by the actuator element 10 of the trigger system, as long as said actuator element is not returned to its rest position, but it is the reservoir 1 which can then be displaced freely so as to enable the valve-member 3 to return to its rest position after the fluid has been dispensed. It is therefore the element which is fixed during actuation (in this case the reservoir 1), which is displaced in order to release the valve member 3.

Thus, in the embodiment shown in FIGS. 1 and 2, when the valve member 3 reaches its dispensing position and delivers the fluid contained in the metering chamber of the metering valve 2, the reservoir 1 is released, the blocking element 20 being able to be displaced towards it unblocking position, the valve member 3 then returning to its rest position, thereby enabling the metering chamber to be filled while the device is still in the user's mouth, and thereby guaranteeing that filling takes place in the required position, as shown in the drawings, with the metering valve 2 disposed beneath the reservoir 1, with filling being achieved by gravity.

In advantageous manner, filling takes place as soon as the previous dose has been dispensed, i.e. very quickly. This prevents any problem of overdosing which could occur if allowed to remain in the upsidedown position, in particular with suspensions.

Advantageously, it is possible to provide a return spring for the blocking element 20, and a return spring for the control element 40, so that when the user returns the actuator element 10 to its rest position, the control element 40 is returned automatically to its initial position by said return spring 44, just as the blocking element 20 is returned to its blocking position by the return spring 24, the retaining member 30 being repositioned inside the groove of said blocking element 20 so as to block said blocking element in the blocking position, and the first diameter 41 of the control member blocking the retaining member in the retaining position.

FIGS. 3 and 4 show a variant embodiment of the release system shown in FIGS. 1 and 2. In this variant, the retaining member is formed by one or a plurality of resilient tabs 30 that are elastically deformable, preferably inwards. The second-diameter portion 42 of the control element 40 is formed by one or a plurality of corresponding openings, enabling said tabs to splay apart, thereby releasing release the blocking element 20.

Although the present invention is described above with reference to several embodiments thereof, which are given by way of non-limiting example, it is clear that the person skilled in the art can apply several modifications thereto without going beyond the ambit of the present invention defined by the accompanying claims.

The invention claimed is:

1. A fluid dispenser device comprising: a reservoir (1) containing the fluid and a propellant; a metering valve (2) mounted on said reservoir and comprising a metering chamber, and a valve member (3) that is movable between a rest position and a dispensing position; and an automatic trigger system, actuated by the user inhaling in order to actuate said valve, said trigger system including an actuator element (10) adapted to displace one of the valve member (3) and the reservoir (1) relative to the other so as to bring the valve member (3) of the valve (2) into its dispensing position, the device being characterized in that it includes, in combination, a brake system (60, 70) which co-operates with the reservoir (1) or with the valve member (3) in order to slow down displacement of the valve member (3) towards its dispensing position during the entire actuation stroke while the device is being actuated, and a valve-member release system that is actuated automatically and immediately when the valve member (3) reaches its dispensing position, and which returns said valve member (3) to its rest position independently of the position of said actuator element (10).

2. A device according to claim 1, in which said brake device (60, 70) is pneumatic and/or hydraulic.

3. A device according to claim 2, in which said brake device (60) comprises a piston (61) connected to said actuator element (10) by means of a control element (40), said piston (61) sliding in sealed manner in a chamber (62), said chamber (62) or said piston (61) being provided with a small passage (63) so that the gas or liquid can flow only slowly into or out of said chamber (62), ensuring that said piston (61) is displaced slowly.

4. A device according to claim 2, in which said brake device (70) comprises a piston (71) connected to said actuator element (10) by means of a control element (40), said piston (71) sliding in non-sealed manner in a chamber (72) so that the air contained in the chamber (72) can flow only slowly out of said chamber (72), ensuring that said piston (71) is displaced slowly.

5. A device according to claim 1, in which said valve-member release system includes a blocking element (20) co-operating with one of the valve member (3) and the fluid reservoir (1), said blocking element (20) being movable between a blocking position, in which the valve member (3) can be brought into its dispensing position by said actuator element (10) of the trigger system, and an unblocking position, in which the valve member (3) is returned to its rest position independently of the position of said actuator element (10), said blocking element (20) being urged towards its unblocking position after the trigger system has been actuated, when the valve member (3) reaches its dispensing position.

6. A device according to claim 5, in which the valve-member release system includes a retaining member (30) that is displaceable between a retaining position, in which it retains said blocking element (20) in its blocking position, and a non-retaining position, in which it does not retain said blocking element (20) in its blocking position, said retaining member (30) being displaced towards its non-retaining position when the valve-member (3) reaches it dispensing position.

7. A device according to claim 6, in which said valve-member release system includes a control element (40) co-operating firstly with the valve member (3) and/or with the actuator element (10), and secondly with said retaining member (30), so that when the valve member (3) reaches its dispensing position, the control member (40) makes it possible to displace the retaining member (30) into its non-retaining position, so that the blocking element (20) is displaced towards it unblocking position and the valve member is returned to its rest position by the return spring of the valve.

8. A device according to claim 7, in which said retaining member (30) is elastically deformable, and said control element includes a first inside diameter (41) co-operating with the retaining member (30) so as to prevent it from deforming, and thus hold it in its retaining position, and a second inside diameter (42) that is greater than said first inside diameter (41), which co-operates with said retaining member (30) when the valve member (3) reaches its dispensing position, thereby enabling said retaining member (30) to deform towards its non-retaining position.

9. A device according to claim 8, in which said retaining member (30) includes one or a plurality of elastically deformable tabs (30).

10. A device according to claim 8, in which the second-diameter portion (42) of the control element (40) is formed by one or a plurality of openings adapted to co-operate with the retaining member (30).

* * * * *